(12) United States Patent
Wittenstein

(10) Patent No.: US 7,063,706 B2
(45) Date of Patent: Jun. 20, 2006

(54) DISTRACTION DEVICE

(75) Inventor: Manfred Wittenstein, Bad Mergentheim (DE)

(73) Assignee: Wittenstein AG, Igersheim (DE)

( * ) Notice: Subject to any disclaimer, the term of this patent is extended or adjusted under 35 U.S.C. 154(b) by 34 days.

(21) Appl. No.: 10/496,057

(22) PCT Filed: Aug. 13, 2002

(86) PCT No.: PCT/EP02/09047

§ 371 (c)(1),
(2), (4) Date: May 19, 2004

(87) PCT Pub. No.: WO03/043512

PCT Pub. Date: May 30, 2003

(65) Prior Publication Data

US 2005/0010233 A1    Jan. 13, 2005

(30) Foreign Application Priority Data

Nov. 19, 2001 (DE) .................. 101 56 316

(51) Int. Cl.
*A61B 17/60* (2006.01)
(52) U.S. Cl. ........................................... 606/90
(58) Field of Classification Search ............... 606/90, 606/95, 98–99, 104–105
See application file for complete search history.

(56) References Cited

U.S. PATENT DOCUMENTS

| | | | | | |
|---|---|---|---|---|---|
| 4,298,074 | A | * | 11/1981 | Mattchen | ............. 173/129 |
| 5,389,072 | A | * | 2/1995 | Imran | ............. 604/95.05 |
| 5,415,660 | A | * | 5/1995 | Campbell et al. | ............. 606/62 |
| 5,490,683 | A | * | 2/1996 | Mickel et al. | ............. 279/75 |
| 5,626,581 | A | * | 5/1997 | Staehlin et al. | ............. 606/63 |
| 5,720,746 | A | * | 2/1998 | Soubeiran | ............. 606/61 |
| 5,972,000 | A | * | 10/1999 | Beyar et al. | ............. 606/139 |
| 6,033,412 | A | * | 3/2000 | Losken et al. | ............. 606/105 |
| 6,264,661 | B1 | * | 7/2001 | Jerger et al. | ............. 606/100 |
| 6,416,516 | B1 | * | 7/2002 | Stauch et al. | ............. 606/62 |
| 6,511,484 | B1 | * | 1/2003 | Torode et al. | ............. 606/104 |
| 6,648,896 | B1 | * | 11/2003 | Overes et al. | ............. 606/90 |
| 6,706,042 | B1 | * | 3/2004 | Taylor | ............. 606/57 |
| 6,730,087 | B1 | * | 5/2004 | Butsch | ............. 606/57 |
| 6,796,984 | B1 | * | 9/2004 | Soubeiran | ............. 606/61 |

FOREIGN PATENT DOCUMENTS

| | | |
|---|---|---|
| GB | 2015440 A | 9/1979 |
| GB | 1558007 A | 12/1979 |
| GB | 2082986 A | 3/1982 |
| GB | 2306413 A | 5/1997 |
| GB | 2311967 A | 10/1997 |
| GB | 2330809 A | 5/1999 |

* cited by examiner

*Primary Examiner*—Eduardo C. Robert
*Assistant Examiner*—Annette Reimers
(74) *Attorney, Agent, or Firm*—Bachman & LaPointe, P.C.

(57) ABSTRACT

A distraction device for moving a one-part or two-part or separated bone apart in order to extend or bridge a bone gap. The device is optionally provided in the form of an intramedullary pin, which can be inserted into a medullary space of a bone and which has at least two elements that can be axially moved in relation to one another. The first element is joined to the second element via at least one detent device for securing a distraction movement, and a pushing module for distracting the first element is assigned to the second element and is joined to the second element in a manner that enables it to be locked.

10 Claims, 1 Drawing Sheet

DISTRACTION DEVICE

BACKGROUND OF THE INVENTION

The present invention relates to a distraction device for moving a one-piece or two-piece or separated bone apart in order to extend or bridge a bone gap, optionally in the form of an intramedullary nail which can be inserted into a medullary space of a bone and has at least two elements which can be moved axially in relation to one another, the first element being connected to the second element via at least one detent device for securing a distraction movement.

Distraction devices of this kind are known and commercially available in a wide variety of designs. They are used primarily to ensure that, when a bone has been cut through, suitable distraction takes place in order to improve endogenous formation of new bone substance. A corresponding distraction device is described in EP 0 346 247 B1, for example, in which an intracorporeal bone intramedullary nail is disclosed which moves two parts of a bone by mechanical means. Such a distraction device is not suitable for very small bones with small cross sections. Moreover, DE 39 21 972 C2 discloses an intramedullary nail which can likewise be lengthened by mechanical means. A disadvantage of the distraction devices known in the prior art is that they are much too large and their degree of efficiency is poor. They can transmit distraction forces to bones only to a limited extent.

A further disadvantage is that distraction devices with a small cross section and with high distraction forces have hitherto been impossible to produce.

EP 0 919 717 A1 describes a drive device with an element made of a shape-memory alloy, and the use thereof. In said document, two pusher modules are moved toward one another, with distraction taking place purely through the compression forces of the shape-memory alloy.

A similar principle is described in the Journal of Physics D. applied physics IOP Publishing, Bristol, GB, volume No. 29, No. 3, of Mar. 14, 1996, pages 923 through 928, in the article entitled "Electromagnetic heating of a shape memory alloy translator". There, a distraction between two pusher modules leads to distraction of a piston, likewise through the action of compression forces generated by a shape-memory alloy.

WO 00/01315 A discloses a distraction device in which, in an actuating device, tensile forces are generated which directly transmit a distraction to a piston via a pusher element 5.

Therefore, it is an object of the present invention to make available a distraction device of the type mentioned at the outset, which avoids the stated disadvantages and with which high distraction forces can be achieved with extremely small external diameters.

SUMMARY OF THE INVENTION

The foregoing object is achieved by the present invention wherein the second element is assigned a pusher module for distraction of the first element, which is connected to the second element so as to permit locking, and a spring element is provided between the pusher module and the second element and exerts pressure on the pusher module, the spring force of the spring element being able to be transmitted for distraction from the pusher module to the first element via a further detent device, and, in order to move the pusher module back and to tension the spring element between pusher module and second element, a compression rod is provided, together with an interposed actuating device.

In the present invention, it is of great importance that one of the two elements is assigned a pusher module which is connected to the other element so as to permit locking.

The pusher module has an actuating device connected to a compression rod so that, when suitably actuated, the pusher module serves to pre-tension a compression spring, in particular a spring element, used for the distraction.

In this connection, it has proven particularly advantageous to use, as the actuating element, shape-memory elements made of shape-memory alloys which shorten in particular when heated, so that very high tensile forces arise. These very high tensile forces are used to move the pusher module back so as to pre-tension the spring element, the return movement taking place relative to the first element and permitting locking, so that a subsequent distraction is effected by the pre-tensioned spring element, which is supported at one end on the wall of a second element and is supported at the other end on an end face of the pusher module, when the shape-memory elements cool and extend again.

The scope of the present invention is also intended to include providing at least one shape-memory element with a suitable heating device, said heating device being supplied with energy via wires (not shown here), for example inductively and subcutaneously, in order to activate the actuating device and spring elements.

In this way, with diameters of very small cross section, it is possible to use spring elements, in particular compression springs, with very high spring constants and spring forces, and very small shape-memory elements with heating elements in the pusher module can be provided in order to pre-tension the spring element by return movement of the pusher module via the actuating device and then, when the spring element exerts pressure on the pusher module, to move the first element and the second element away from one another with the combined action of the second detent device.

It is important that the shape-memory elements move the pusher module back by applying tension in order to pre-tension the spring element, so that very high pre-tensioning forces can be realized here by means of the actuating device. Moreover, a construction of this kind also permits a distraction device of small length and extremely small overall cross section, which likewise is intended to lie within the scope of the present invention.

BRIEF DESCRIPTION OF THE DRAWINGS

Further advantages, features and details of the invention will become evident from the following description of a preferred illustrative embodiment where, in the single FIGURE, a diagrammatic cross-sectional view is shown of a distraction device R according to the invention in a use position.

DETAILED DESCRIPTION

Figure 1:
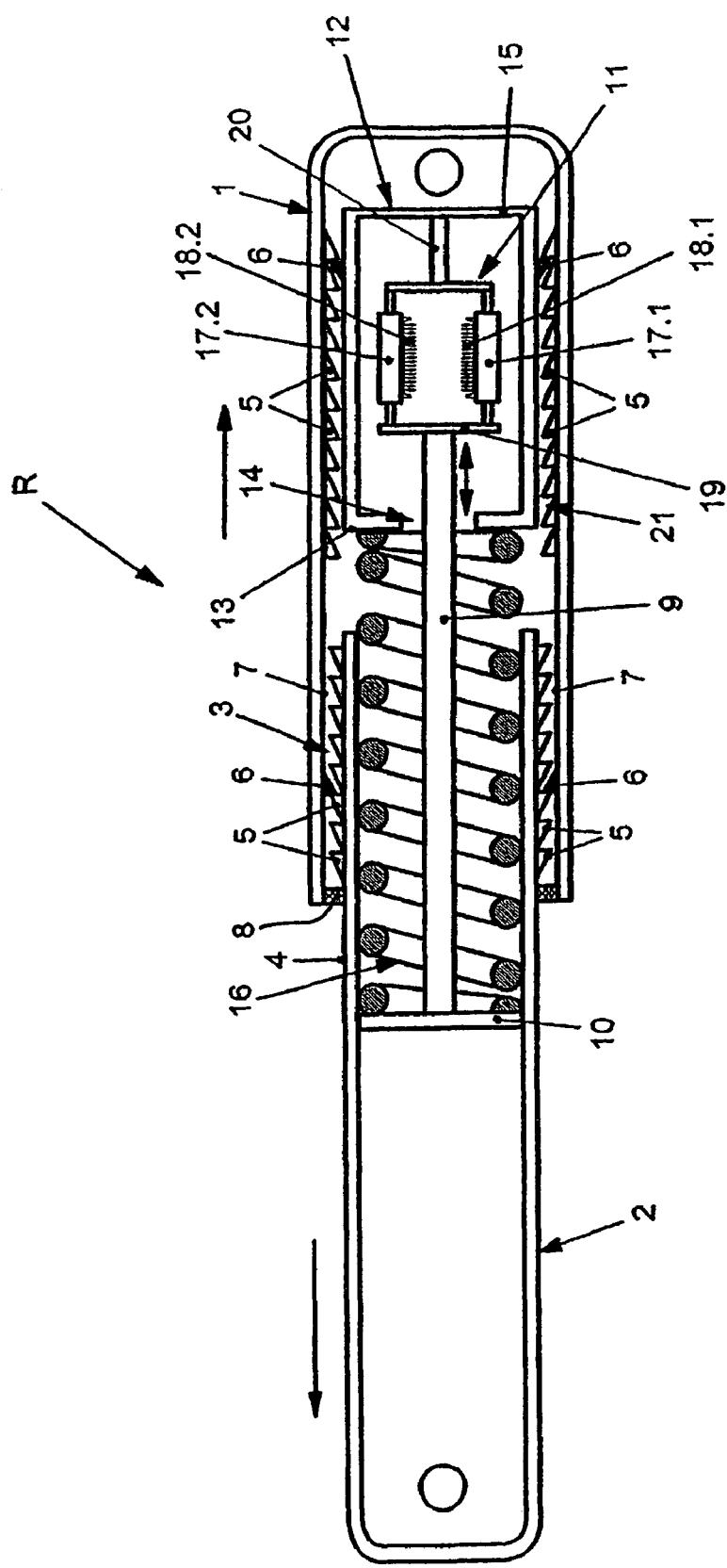

In FIG. 1, a distraction device R according to the invention has two elements 1, 2 which can be moved relative to one another, the element 2 preferably being able to be pushed as a tube into the element 1. A first detent device 3 has, on an outer surface 4 of the element 2, detent lugs 5 in which at least one catch 6 of the element 1 engages. The catch 6 is preferably assigned to an inner wall 7 of the element 1 or is formed by this.

The detent device 3 permits a distraction movement of the element 1 and of the element 2 away from one another in the direction of the arrows illustrated, but not a movement in toward one another. In the latter case, the catch 6 engages between the detent lugs 5 and blocks any movement toward one another of element 1 and element 2. Only a distraction, i.e. a movement of element 1 and element 2 away from one another, is guaranteed by the arrangement of the detent device 3.

A seal 8 seals off the annular gap formed between element 1 and element 2.

Another important aspect of the present invention is that, inside the element 2, a compression rod 9 is provided which is supported on a wall 10 in the element 2 and is fixed thereon and preferably extends out from the element 2 at one end.

Adjoining one end of the compression rod 9 there is an actuating device 11, which is connected at one end to a pusher module 12.

The pusher module 12 is preferably designed as a tubular element and at one end in the region of an end face 13 is provided with an opening 14 through which the compression rod 9 engages.

Inside the pusher module 12, the actuating device 11 is fitted between the compression rod 9 and an end wall 15.

Another important aspect of the present invention is that at least one spring element 16 extends between the end face 13 of the pusher module 12 and the wall 10 of the element 2, the ends of said spring element 16 being supported on the wall 10 and on the end face 13, respectively. The spring element 16 is preferably guided axially via the compression rod 9.

The actuating device 11 consists of at least one shape-memory element 17.1, 17.2 made of a shape-memory alloy, and at least one heating element 18.1, 18.2 assigned thereto. The heating element 18.1, 18.2 can be operated via electrical leads (not shown here) and can heat the shape-memory elements 17.1, 17.2.

The heating elements 18.1, 18.2 can be controlled inductively and subcutaneously, for example, in order to activate the actuating device 11 and the shape-memory elements 17.1, 17.2 made of shape-memory alloys.

The function of the present invention is as follows:

When the shape-memory element 17.1, 17.2 is heated by means of the heating element 18.1, 18.2, the shape-memory elements 17.1, 17.2 shorten considerably.

At one end, the shape-memory elements 17.1, 17.2 are supported via a plate 19 and, together with the connection element 20 connected to the end wall 15, they draw the pusher module 12 toward the wall 10 or toward the spring element 16.

While the pusher module 12 is moved toward the wall 10 of the element 2 upon heating of the shape-memory elements 17.1, 17.2, the element 1 remains fixed via the first detent device 3.

A second detent device 21 ensures that at least one catch 6 of the pusher module 12 engages in corresponding detent lugs 5 provided on the inner wall 7 of the element 1. The pusher module 12 can be moved only by means of the actuating device 11 or shape-memory elements 17.1, 17.2 toward the wall 10 or toward the spring element 16 and tensions the latter. A return movement is prevented by the second detent device 21 and via the catch 6 and the detent lugs 5 engaging in the latter. In this way, it is possible to tension the spring element 16 very easily and effectively, which, upon cooling and corresponding lengthening of the actuating device 11 and of the shape-memory elements 17.1, 17.2, permits a distraction of the element 1 relative to the element 2, with the spring element 16 being pre-tensioned and having pressure exerted on it toward the end face 13 of the pusher module 12, and the pusher module 12, via the catch 6, moving the first element 1 and the second element 2 away from one another to permit distraction.

After suitable distraction, it is then possible, as has been described above, to shorten the actuating device 11 and the shape-memory elements 17.1, 17.2 in order to move the pusher module 12 back relative to the element 1 in the above-described manner, in order to once again pre-tension the spring element 16. This procedure can be repeated as many times as is needed.

An advantage of the present invention is that very small diameters of distraction devices R can be realized, and very strong spring elements 16 with a high spring constant can be used. Moreover, by shortening of the shape-memory elements 17.1, 17.2, very high tensile forces can be generated for moving the pusher module 12 back and pre-tensioning the spring element 16, which likewise contributes considerably to minimizing the overall diameter of the distraction device R.

The invention claimed is:

1. A distraction device for bridging a bone gap, comprises at least two elements movable relative to one another, wherein the first element (1) is connected to the second element (2) by at least one detent means (3) for securing a distraction movement, and the second element (2) is assigned a pusher module means (12) for distraction of the first element (1), which is connected to the second element (2) so as to permit locking, a spring element (16) is provided between the pusher module means (12) and the second element (2) and exerts pressure on the pusher module means (12), wherein, in order to move the pusher module means (12) back and to tension the spring element (16) between pusher module (12) and second element (2), a compression rod (9) is provided, together with an actuating device (11) interposed between the compression rod (9) and the push module means (12), the actuating device (11) comprises at least one shape-memory element (17.1, 17.2) and a heating device (18.1, 18.2).

2. The distraction device as claimed in claim 1, wherein the spring force of the spring element (16) being able to be transmitted for distraction from the pusher module means (12) to the first element (1) by a second detent means (21).

3. The distraction device as claimed in claim 2, wherein the second detent means (21) transmits distraction movement of the pusher module means (12) to the first element (1) in a blocking manner and transmits a distraction movement for distraction of the first element (1) relative to the second element (2), which element (1) can be driven and locked relative to the element (2) by means of the first detent means (3).

4. The distraction device as claimed in claim 1, wherein the actuating device (11) is arranged inside the pusher module means (12), and the compression rod (9) engages the actuating device in the pusher module means (12).

5. The distraction device as claimed in claim 1, wherein, by heating the shape-memory element (17.1, 17.2) by means of the heating device (18.1, 18.2), a shortening of the shape-memory element (17.1, 17.2) takes place, which results in the pusher module means (12) being moved back relative to the first element (1), and a movement of the first element (1) relative to the second element (2) is blocked via the at least one detent means (3).

6. The distraction device as claimed in claim 5, wherein, after the shape-memory element (17.1, 17.2) has been cooled, a lengthening of the actuating device (11) takes place, and, when the second element (2) exerts pressure on the pusher module means (12) by the spring element (16), a distraction of the first element (1) relative to the second element (2) takes place.

7. The distraction device as claimed in claim 5, wherein, by heating at least one shape-memory element (17.1, 17.2), the pusher module means (12) can be moved toward the spring element (16), drives the latter toward the second element (2) and thus tensions the spring element (16), and a return movement of the pusher module means (12) in the direction of distraction is blocked by means of the second detent means (21).

8. The distraction device as claimed in claim 1, wherein at least two shape-memory elements (17.1, 17.2), each with a heating device (18.1, 18.2), are arranged between compression rod (9) and pusher module means (12).

9. The distraction device as claimed in claim 1, wherein the spring element (16) encircles the compression rod (9) and is supported at one end on the pusher module means (12) and at the other end on the second element (2).

10. The distraction device as claimed in claim 1, wherein the at least one shape-memory element (17.1, 17.2) is supported at one end on the compression rod (9) and at the other end directly on one of the pusher module means (12) and an end face (13) of the pusher module means (12).

* * * * *